(12) United States Patent
Bode et al.

(10) Patent No.: US 7,667,076 B2
(45) Date of Patent: Feb. 23, 2010

(54) AMIDE FORMING CHEMICAL LIGATION

(75) Inventors: Jeffrey W. Bode, Santa Barbara, CA (US); Ryan M. Fox, Santa Barbara, CA (US)

(73) Assignee: Regents of the University of California, Oakland, CA (US)

( * ) Notice: Subject to any disclaimer, the term of this patent is extended or adjusted under 35 U.S.C. 154(b) by 438 days.

(21) Appl. No.: 11/227,950

(22) Filed: Sep. 14, 2005

(65) Prior Publication Data

US 2007/0060773 A1    Mar. 15, 2007

(51) Int. Cl.
*C07C 231/02* (2006.01)
(52) U.S. Cl. ....................... 564/138; 548/240
(58) Field of Classification Search ................. 548/240; 564/138
See application file for complete search history.

(56) References Cited

U.S. PATENT DOCUMENTS 5,103,055 A * 4/1992 Cesa ........................... 564/130

FOREIGN PATENT DOCUMENTS

EP          0 635 488    *    1/1995

OTHER PUBLICATIONS

Ahmad et al, Canadian Journal of Chemistry, vol. 30, 1340-1359, 1961.*

* cited by examiner

*Primary Examiner*—Shailendra Kumar
(74) *Attorney, Agent, or Firm*—Richard Aron Osman

(57) ABSTRACT

An amide is formed by reacting an α-ketoacid or salt thereof in a decarboxylative condensation reaction with an amine or salt thereof comprising a nitrogen covalently bound to an atom selected from oxygen, nitrogen, and sulfur. The amide bond is formed between the α-carbon of the ketoacid and the nitrogen of the amine. The α-ketoacid can be formed using a novel sulfur reagent.

28 Claims, No Drawings

AMIDE FORMING CHEMICAL LIGATION

FIELD OF THE INVENTION

The field of the invention is a decarboxylative condensation reaction between an α-ketoacid and an amine to form an amide.

BACKGROUND OF THE INVENTION

Despite the ubiquity and importance of amide bonds, there are surprisingly few mechanistically distinct approaches to their preparation. For intermolecular couplings, amides are almost uniformly synthesized by the addition of an amine to an activated carboxylate. [1] This paradigm, which employs carboxylic acids and amines as starting materials, enables the widely employed methods of solid phase peptide synthesis and constitutes the basis for peptide assembly in biological systems. The notoriously poor functional group tolerance and chemoselectivity issues of condensation approaches have encouraged novel solutions to direct amidations with unprotected fragments under aqueous conditions. In this regard, the recent identification of the native peptide ligation reaction, which allows the chemoselective union of an N-terminal cysteine or related derivative and C-terminal thioesters, [2, 3] has dramatically impacted the synthetic accessibility of modified proteins and other complex amide based-structures. While important and widely used, this thioester ligation process is inherently constrained to substrates containing a free N-terminal sulfhydryl and more general alternatives are in great demand. [4,5]

An ideal peptide ligation would provide amide bonds by the direct coupling of unprotected precursors containing familiar but orthogonally reactive functional groups under aqueous conditions and without reagents, catalysts, or by-products. We now document this goal by the direct coupling of α-ketoacids and amine derivatives to afford native peptide bonds under mild, reagent-free conditions, producing only carbon dioxide and water or alcohol as by-products.

SUMMARY OF THE INVENTION

One aspect of the invention is a method of forming an amide, the method comprising the step of: reacting an α-ketoacid or salt thereof in a decarboxylative condensation reaction with an amine or salt thereof comprising a nitrogen covalently bound to an atom selected from oxygen, nitrogen, and sulfur; whereby an amide bond is formed between the α-carbon of the ketoacid and the nitrogen of the amine.

In one embodiment, the α-ketoacid has the structure of formula (1):

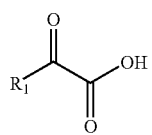

(1)

the amine has the structure of formula (2):

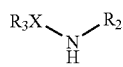

(2)

and the amide has the structure of formula (3):

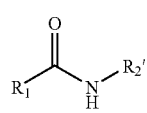

(3)

wherein $R_1$ and $R_2$ are independently selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety; X is selected from an oxygen atom, a nitrogen atom, and a sulfur atom; $R_3$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, and a bond that joins X to $R_2$ that, taken together with the nitrogen atom, forms an optionally substituted heterocyclic ring of 4 to 7 atoms; and $R_2'$ is $R_2$ or, when $R_3$ is a bond, the ring-opening reaction product of $R_2$.

In one embodiment the amine has the structure of formula (4):

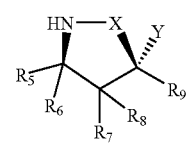

(4)

wherein X is selected from an oxygen atom, a nitrogen atom, and a sulfur atom; Y is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, optionally substituted oxyalkyl group, optionally substituted oxyaryl, optionally substituted thioalkyl, and optionally substituted thioaryl; and $R_5$ through $R_9$ are independently selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, oxygen, nitrogen, and a bond that joins with a different one of said $R_5$ through $R_9$ to form a ring.

In certain embodiments the amine is selected from an isoxazolidine, an N-alkylhydroxylamine, an N,O-dialkylhydroxylamine, an N-alkyl, O-acylhydroxylamine, and a peptide hydroxylamine.

In particular embodiments the reaction is not dependent upon additional reagent or catalyst. In certain embodiments the principal by-products produced by the reaction are water and CO2 or an alcohol and CO2.

In certain embodiments, the reaction occurs at 0° C.-150° C., and preferably at 25° C.-75° C.

In another embodiment, the reaction occurs on a solid phase.

In a further embodiment, prior to the reacting step, the α-ketoacid is synthesized by combining a carboxylic acid of formula (5):

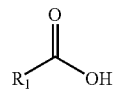

(5)

with a sulfur reagent of formula (6):

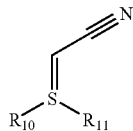
(6)

or a salt thereof under reaction conditions to form a sulfur ylide of formula (7):

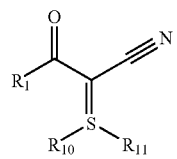
(7)

and contacting the sulfur ylide with an oxidizer and water to form the α-ketoacid; wherein $R_1$ is defined as above; $R_{10}$ is selected from optionally hetero-, optionally substituted alkyl, and optionally hetero-, optionally substituted aryl; and $R_{11}$ is selected from optionally hetero-, optionally substituted alkyl, optionally hetero-, optionally substituted aryl, and a bond that joins $R_{10}$ to form an optionally substituted heterocyclic ring of 4 to 7 atoms.

In particular embodiments, the sulfur reagent has formula (8):

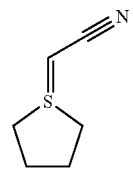
(8)

and the sulfur ylide has formula (9):

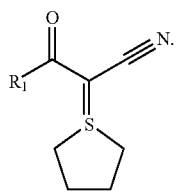
(9)

Another aspect of the invention is a compound of formula (10):

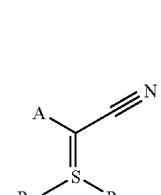
(10)

or a salt thereof, wherein A is a hydrogen atom or $C(O)R_1$; and $R_1$, $R_{10}$, and $R_{11}$ are defined as above.

In one embodiment of the compound $R_{11}$ is a bond that joins $R_{10}$ to form a thiolane or thiane ring.

In another embodiment, A is a hydrogen atom, $R_{10}$ is a C5-C6 alkyl, and $R_{11}$ is a bond that joins $R_{10}$ to form a thiolane or thiane ring.

In a further embodiment of the compound, A is a hydrogen atom, $R_{10}$ is a C5-C6 alkyl substituted with a C0-C6 alkyl carboxylic acid, and $R_{11}$ is a bond that joins $R_{10}$ to form a thiolane or thiane ring substituted with a C0-C6 alkyl carboxylic acid.

In another embodiment, the compound is attached to a solid phase.

In one embodiment of the compound $R_1$ is a peptide moiety.

A further aspect of the invention is a method of making the compound of formula 10 wherein A is a hydrogen atom, and the method comprises reacting a thioether with a halogenonitrile to form the compound, and recovering the compound. In preferred embodiments, the halogenonitrile is selected from the group consisting of chloroacetonitrile, bromoacetonitrile, and iodoacetonitrile.

Another aspect of the invention is a method of synthesizing an α-ketoacid comprising the steps of: combining a carboxylic acid of formula (5):

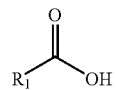
(5)

with a sulfur reagent of formula (6):

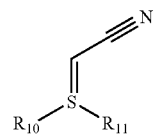
(6)

or a salt thereof under reaction conditions to form a sulfur ylide of formula (7):

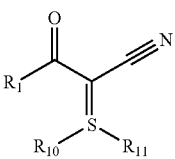
(7)

and contacting the sulfur ylide with an oxidizer and water to form an α-ketoacid of formula (1):

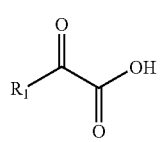
(1)

wherein $R_1$, $R_{10}$, and $R_{11}$ are as defined above.

DETAILED DESCRIPTION OF SPECIFIC EMBODIMENTS OF THE INVENTION

One aspect of the invention is a novel decarboxylative condensation reaction of an alpha-ketoacid and an amine derivative that provides a method for the direct, reagent-free synthesis of an amide under organic or aqueous conditions that requires no additional reagents or catalysts. The method comprises the step of reacting an α-ketoacid or salt thereof with an amine or salt thereof, wherein the amine comprises a nitrogen atom covalently bound to an oxygen, nitrogen, or sulfur atom; and wherein the amide bond is formed between the α-carbon of the ketoacid and the nitrogen of the amine.

In one embodiment, the α-ketoacid has the structure of formula (1):

(1)

the amine has the structure of formula (2):

(2)

and the amide has the structure of formula (3):

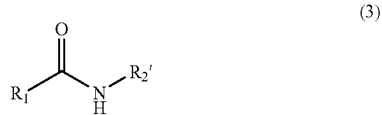

(3)

In the above structures, $R_1$ and $R_2$ are independently selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety; X is selected from oxygen, nitrogen, and sulfur; $R_3$ is selected from hydrogen, optionally hetero-, optionally substituted alkyl, optionally hetero-, optionally substituted alkenyl, optionally hetero-, optionally substituted alkynyl, optionally hetero-, optionally substituted aryl; optionally hetero-, optionally substituted arylalkyl, optionally hetero-, optionally substituted acyl, and a bond that joins X to $R_2$ that, taken together with the nitrogen atom, forms a optionally substituted heterocyclic ring of 4 to 7 atoms; and $R_2'$ is $R_2$ or, when $R_3$ is a bond, the ring-opening reaction product of $R_2$. An example of a ring-opening reaction product of $R_2$ is shown in the reaction scheme below where the amine is an isoxazolidine of formula 15.

As used herein, the term "heteroatom" includes oxygen (O), nitrogen (N), sulfur (S) and silicon (Si).

The term "alkyl," by itself or as part of another substituent, means, unless otherwise stated, a straight or branched chain, or cyclic hydrocarbon radical, or combination thereof, which is fully saturated, having the number of carbon atoms designated (i.e. C1-C8 means one to eight carbons). Examples of alkyl groups include methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl and the like.

The term "alkenyl", by itself or as part of another substituent, means a straight or branched chain, or cyclic hydrocarbon radical, or combination thereof, which may be mono- or polyunsaturated, having the number of carbon atoms designated (i.e. C2-C8 means two to eight carbons) and one or more double bonds. Examples of alkenyl groups include vinyl, 2-propenyl, crotyl, 2-isopentenyl, 2-(butadienyl), 2,4-pentadienyl, 3-(1,4-pentadienyl) and higher homologs and isomers thereof.

The term "alkynyl", by itself or as part of another substituent, means a straight or branched chain hydrocarbon radical, or combination thereof, which may be mono- or polyunsaturated, having the number of carbon atoms designated (i.e. C2-C8 means two to eight carbons) and one or more triple bonds. Examples of alkynyl groups include ethynyl, 1- and 3-propynyl, 3-butynyl and higher homologs and isomers thereof.

The term "alkylene" by itself or as part of another substituent means a divalent radical derived from alkyl, as exemplified by —CH2-CH2-CH2-CH2-. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —CH2-CH2-O—CH3, —CH2-CH2-NH—CH3, —CH2-CH2-N(CH3)-CH3, —CH2-S—CH2-CH3, —CH2-CH2, —S(O)—CH3, —CH2-CH2-S(O)$_2$—CH3, —CH=CH—O—CH3, —Si(CH3)$_3$, —CH2-CH=N—OCH3, and —CH=CH—N(CH3)-CH3. Up to two heteroatoms may be consecutive, such as, for example, —CH2-NH—OCH3 and —CH2-O—Si(CH3)$_3$.

Similarly, the term "heteroalkylene," by itself or as part of another substituent means a divalent radical derived from heteroalkyl, as exemplified by —CH2-CH2-S—CH2-CH2- and —CH2-S—CH2-CH2-NH—CH2-. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Accordingly, a cycloalkyl group has the number of carbon atoms designated (i.e., C3-C8 means three to eight carbons) and may also have one or two double bonds. A heterocycloalkyl group consists of the number of carbon atoms designated and from one to three heteroatoms selected from the group consisting of O, N, Si and S, and wherein the nitrogen and sulfur atoms may optionally be oxidized and the nitrogen heteroatom may optionally be quaternized. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5, 6-tetrahydropyrid-yl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" and "halogen," by themselves or as part of another substituent, mean, unless otherwise stated, a fluorine, chlorine, bromine, or iodine atom. Additionally, terms such as "haloalkyl," are meant to include alkyl substituted with halogen atoms, which can be the same or different, in a number ranging from one to (2m'+1), where m' is the total number of carbon atoms in the alkyl group. For example, the term "halo(C1-C4)alkyl" is meant to include trifluoromethyl, 2,2,2-trifluoroethyl, 4-chlorobutyl, 3-bromopropyl, and the like. Thus, the term "haloalkyl" includes monohaloalkyl (alkyl substituted with one halogen atom) and polyhaloalkyl (alkyl substituted with halogen atoms in a number ranging from two to (2m'+1) halogen atoms, where m' is the total number of carbon atoms in the alkyl group). The term "perhaloalkyl" means, unless otherwise stated, alkyl substituted with (2m'+1) halogen atoms, where m' is the total number of carbon atoms in the alkyl group. For example the term "perhalo(C1-C4)alkyl" is meant to include trifluoromethyl, pentachloroethyl, 1,1,1-trifluoro-2-bromo-2-chloroethyl and the like.

The term "acyl" refers to those groups derived from an organic acid by removal of the hydroxy portion of the acid. Accordingly, acyl is meant to include, for example, acetyl, propionyl, butyryl, decanoyl, pivaloyl, benzoyl and the like. Acyl groups have the general formula R—C(=O)Y where R is a bond or alkyl of 1-12 C-atoms, and Y is selected from a hydrogen atom (aldehydes), alkyl (ketones), NH or N-alkyl (amides), O-alkyl (esters), OH (carboxylic acids), OCO-alkyl (anhydrides), and a halogen (acyl halides).

The term "aryl" means, unless otherwise stated, a polyunsaturated, typically aromatic, hydrocarbon substituent which can be a single ring or multiple rings (up to three rings) which are fused together or linked covalently. Non-limiting examples of aryl groups include phenyl, 1-naphthyl, 2-naphthyl, 4-biphenyl, 1,2,3,4-tetrahydronaphthalene, indolyl, indanyl and indenyl.

The term heteroaryl," refers to aryl groups (or rings) that contain from zero to four heteroatoms selected from N, O, and S, wherein the nitrogen and sulfur atoms are optionally oxidized and the nitrogen heteroatom are optionally quaternized. A heteroaryl group can be attached to the remainder of the molecule through a heteroatom. Non-limiting examples of heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl and 6-quinolyl.

The term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") is meant to include both substituted and unsubstituted forms of the indicated radical. Preferred substituents for each type of radical are provided below.

Substituents for the alkyl and heteroalkyl radicals (as well as those groups referred to as alkylene, alkenyl, heteroalkylene, heteroalkenyl, alkynyl, cycloalkyl, heterocycloalkyl, cycloalkenyl and heterocycloalkenyl) can be a variety of groups selected from: —OR', =O, =NR', =N—OR', —NR'R", =N, =S, —SR', halogen, —SiR'R"R'", —OC(O)R', —C(O)R', —CO2R', —CONR'R", —OC(O)NR'R", —NR"C(O)R', —NR'—C(O)NR"R'", —NR'—SO2NR"', —NR"CO2R', —NH—C(NH2)=NH, —NR'C(NH2) =NH, —NH—C(NH2)=NR', —S(O)R', —SO2R', —SO2NR'R", —NR"SO2R, —CN and —NO2, in a number ranging from zero to three, with those groups having zero, one or two substituents being particularly preferred. R', R" and R'" each independently refer to hydrogen, unsubstituted (C1-C8)alkyl and heteroalkyl, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. For example, —NR'R" is meant to include 1-pyrrolidinyl and 4-morpholinyl. Typically, an alkyl or heteroalkyl group will have from zero to three substituents, with those groups having two or fewer substituents being preferred in the present invention. More preferably, an alkyl or heteroalkyl radical will be unsubstituted or monosubstituted. Most preferably, an alkyl or heteroalkyl radical will be unsubstituted. From the above discussion of substituents, one of skill in the art will understand that the term "alkyl" is meant to include groups such as trihaloalkyl (e.g., —CF3 and —CH2CF3).

Similarly, substituents for the aryl and heteroaryl groups are varied and selected from: halogen, —OR', —OC(O)R', —NR'R", —SR', —R', —CN, —NO2, —CO2R', —CONR'R", —C(O)R', —OC(O)NR'R", —NR"C(O)R', —NR"CO2R', —NR'—C(O)NR"R'", —NR'—SO2NR"R'", —NH—C(NH2)=NH, —NR'C(NH2)=NH, —NH—C(NH2)=NR', —S(O)R', —SO2R', —SO2NR'R", —NR"SO2R, —N3, —CH(Ph)2, perfluoro(C1-C4)alkoxy and perfluoro(C1-C4)alkyl, in a number ranging from zero to the total number of open valences on the aromatic ring system; and where R', R" and R'" are independently selected from hydrogen, (C1-C8)alkyl and heteroalkyl, unsubstituted aryl and heteroaryl, (unsubstituted aryl)-(C1-C4)alkyl and (unsubstituted aryl)oxy-(C1-C4)alkyl. Typically, an aryl or heteroaryl group will have from zero to three substituents, with those groups having two or fewer substituents being preferred. In one embodiment of the invention, an aryl or heteroaryl group will be unsubstituted or monosubstituted.

The X and R-groups are reaction compatible, and may optionally comprise protecting groups commonly used in organic synthesis (see e.g. Spivey & Maddaford, Annu. Rep. Prog. Chem., Sect. B, 1999, 95: 83-95). For example, in the case where $R_1$ and/or $R_2$ is an amino acid or peptide moiety, the amino acid(s) may optionally have side chain protecting groups (e.g. 9-fluorenylmethoxycarbonyl (Fmoc), t-Butyl (tBu), etc.). The ligation reactions can be executed on both protected and unprotected peptide moieties and standard protecting groups do not interfere with the ligation chemistry.

In a particular embodiment of the amine where $R_3$ is bond that joins X to $R_2$, the heterocyclic ring has 5 to 6 atoms. The structure of formula (4) is exemplary:

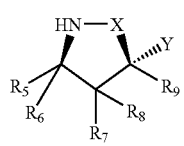

(4)

wherein Y is selected from hydrogen, optionally hetero-, optionally substituted alkyl, optionally hetero-, optionally substituted arylalkyl, optionally hetero, optionally substituted aryl, optionally substituted oxyalkyl, optionally substituted oxyaryl, optionally substituted thioalkyl, and optionally substituted thioaryl; and $R_5$ through $R_9$ are independently selected from hydrogen, optionally hetero, optionally substituted alkyl, optionally hetero, optionally substituted aryl, optionally hetero, optionally substituted acyl, oxygen, nitrogen, and a bond that joins with a different one of said $R_5$ through $R_9$ to form a ring.

In a preferred embodiment where the amine has the structure of formula 4, $R_5$ is an amino acid side-chain group or an alkyl joined to an amino acid side chain group (see e.g. structure 12 below), $R_6$ through $R_8$ are hydrogen atoms, Y is an oxyalkyl group, and $R_9$ is an ester group. Exemplary amines having this structure include the following isoxazolidines (compounds 11-13) which we have synthesized in enantiomerically pure form by nitrone cycloadditions:

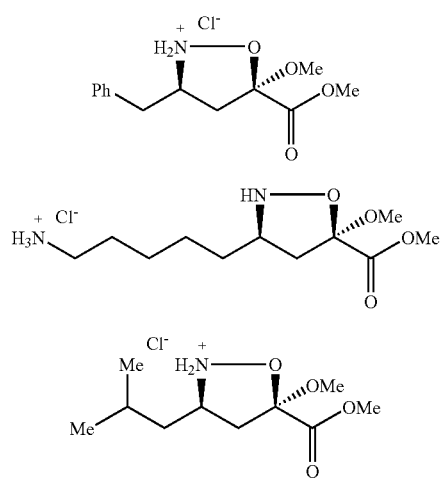

11

12

13

An exemplary reaction using an isoxazolidine substrate is shown below:

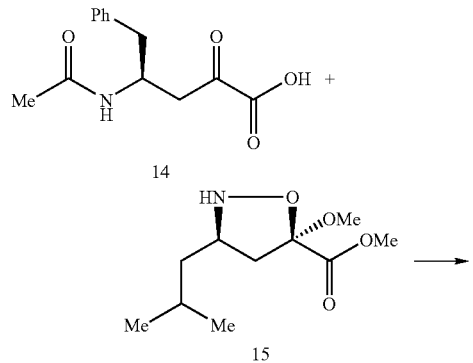

14

15

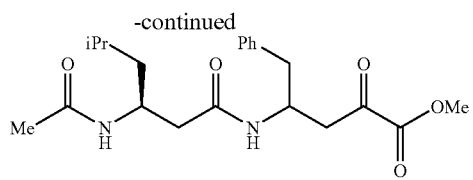

16

In another embodiment, the amine used in the method is selected from an N-alkylhydroxylamine, an N,O-dialkylhydroxylamine, an N-alkyl, O-acylhydroxylamine, and a peptide hydroxylamine. In yet another preferred embodiment of the amine, $R_2$ is a carbohydrate moiety such as a pyranose or a furanose. The preparation of exemplary amines is shown in Example 3.

In our decarboxylative condensation reaction the α-ketoacid and amine can be directly coupled under mild conditions to afford a native peptide bond without additional reagent or catalyst such that, depending upon the amine reactant used, the principal by-products produced by the reaction are water and $CO_2$ or an alcohol and $CO_2$. The reaction is typically allowed to occur at a temperature range of 0° C.-150° C., and more typically at a temperature range of 25° C.-75° C. A variety of suitable reaction conditions is detailed in Example 1, Table 1.

In one embodiment, the reaction occurs on a solid phase. For example, the α-ketoacid can be prepared using a sulfur ylide reagent attached to a solid phase, such as an amine resin (see structure 19 below).

Another aspect of the invention is a method of synthesizing an α-ketoacid that can be used as a reactant in the above-described method of forming an amide. The method for synthesizing the α-ketoacid comprises the steps of combining a carboxylic acid of formula (5):

$$\underset{R_1}{\overset{O}{\|}}\text{—OH}$$ (5)

with a sulfur reagent of formula (6):

(6)

or a salt thereof under reaction conditions to form a sulfur ylide of formula (7):

(7)

and contacting the sulfur ylide with an oxidizer and water to form an α-ketoacid of formula (1):

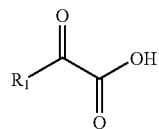
(1)

wherein $R_1$ has the same description as provided above; $R_{10}$ is selected from optionally hetero-, optionally substituted alkyl, and optionally hetero-, optionally substituted aryl; and $R_{11}$ is selected from optionally hetero, optionally substituted alkyl, optionally hetero-, optionally substituted aryl, and a bond that joins $R_{10}$ to form an optionally substituted heterocyclic ring of 4 to 7 atoms.

Suitable oxidizers that can be used in the reaction include Dupont's Oxone®, mCPBA, dimethyldioxarane (DMDO), ozone, bleach (NaOCl), tertiary amine oxides, magnesium monoperphthalate, hydrogen peroxide, etc. Exemplary reaction conditions for synthesis of the α-ketoacid are detailed in Example 2. In particular embodiments, $R_1$ is a di-, tri-, or tetra-peptide.

In particular embodiments, the sulfur reagent has the formula (8):

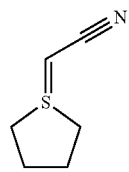
(8)

or a salt thereof and the sulfur ylide has the formula (9):

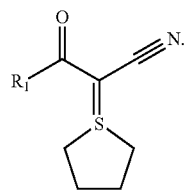
(9)

Another aspect of the invention is a sulfur reagent or sulfur ylide as described above, or a salt thereof, that is generically represented by formula (10):

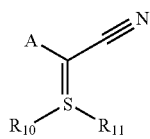
(10)

wherein A is a hydrogen atom or $C(O)R_1$ and $R_1$, $R_{10}$, and $R_{11}$ are as described above. In certain preferred embodiments $R_1$ is a peptide moiety. In a particular embodiment, $R_{11}$ is a bond that joins $R_{10}$ to form a thiolane or thiane ring. In a further embodiment, A is a hydrogen atom, $R_{10}$ is a C5-C6 alkyl, and $R_{11}$ is a bond that joins $R_{10}$ to form a thiolane or thiane ring. In one embodiment the compound is attached to a solid phase. Thiolane or thiane rings substituted with a C0-C6 alkyl carboxylic acid are particularly suitable for solid phase attachment. In a particular embodiment, A is a hydrogen atom, $R_{10}$ is a C5-C6 alkyl substituted with a C0-C6 alkyl carboxylic acid, and $R_{11}$, is a bond that joins $R_{10}$ to form a thiolane or thiane ring substituted with a C0-C6 alkyl carboxylic acid. Specific sulfur reagents having the general formula 10 include the following:

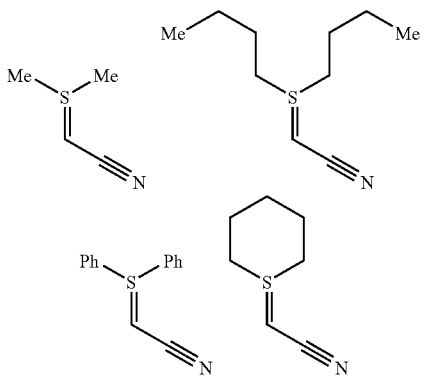

Compounds 17 and 18 are exemplary structures for use in solid phase synthesis (n=0-6):

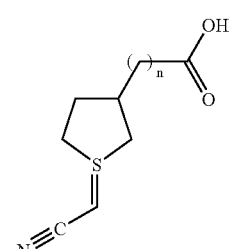
17

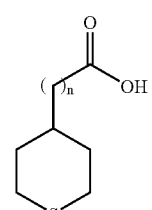
18

These structures can be readily used as linkers to modify existing resins, for example, by attachment to an amine resin as depicted in structure 19, which can be subsequently oxidized to the α-ketoacid and used in solid phase amide synthesis:

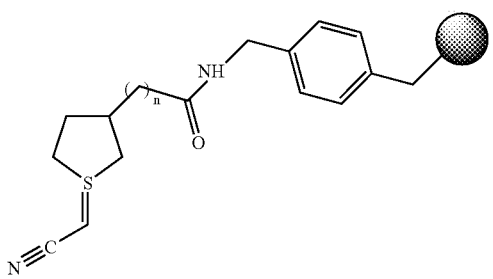

The sulfur reagent can be prepared by reacting a corresponding thioether with a halogenonitrile to form the compound, and recovering the compound. Preferred halogenonitriles are chloroacetonitrile, bromoacetonitrile, and iodoacetonitrile. Exemplary reaction conditions for synthesis of the sulfur reagent are detailed in Example 2. The salts of the above-described sulfur reagents have a positively charged sulfur atom (and single bond linking the sulfur atom to the acetonitrile group) and a counterion (e.g. $Br^-$, $Cl^-$, $I^-$, $TfO^-$, $ClO_4^-$, $BF_4^-$, $AcO^-$, $CF_3O^-$, $PF_6^-$, etc).

Example 1

Decarboxylative Condensations of α-Ketoacids and N-Alkylhydroxylamines

We show the direct coupling of α-ketoacids and N-alkylhydroxylamines to afford native peptide bonds under mild, reagent-free conditions, producing only water and carbon dioxide as by-products (eq. 1):

Equation 1:

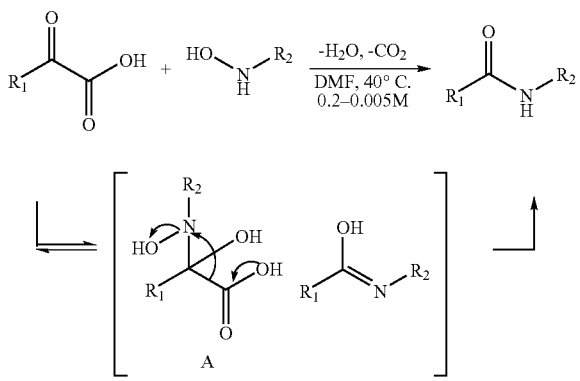

This decarboxylative amidation evolved from the recognition that while the condensation of carboxylic acids and amines to give amides is kinetically and thermodynamically unfavorable, the related condensation of carbonyls and N-alkylhydroxylamines, affording nitrones, is generally an efficient process. Ketones rarely condense with hydroxylamines to give the corresponding nitrones under mild conditions, but instead form metastable hemiaminals. [6] We reasoned that reaction of N-alkylhydroxylamines and α-ketoacids would produce A, in the above reaction scheme, which could undergo decarboxylative dehydration to the desired amide product. The synthesis of other carboxylic acid derivatives by oxidative decarboxylations of α-ketoacids has been described previously. [7]

No reagents, catalysts, dehydrating reagents, or additives are required. The reaction progress reveals clean formation of the amide product, and the reactions are generally complete within 15 h. For the reaction solvent, other polar solvents including DMSO, $CH_3CN$, NMP, and MeOH have been equally efficient as DMF. Furthermore, amide bond formations occurred under aqueous conditions using either suspensions in pure $H_2O$ or aqueous buffers or in soluble mixtures of $H_2O$ or buffers with DMSO or DMF as cosolvent. We typically conduct the ligation reactions in aqueous DMSO or DMF at 0.1 M concentration, however reactant concentrations as low as 0.001 M are viable without detrimental decreases in the reaction time. Conveniently, either the free ketoacids and hydroxylamines or their corresponding salts are suitable starting materials.

The coupling of two representative substrates, phenylpyruvic acid (20) and N-phenethylhydroxylamine (21) demonstrates the facility of this process (eq. 1a).

Equation 1a:

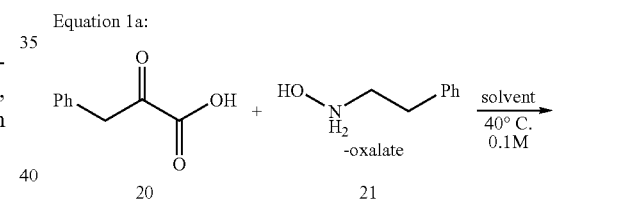

TABLE 1

Reaction conditions for decarboxylative amide ligations

| Entry | conditions[a] | time (h) | yield[b] (%) |
|---|---|---|---|
| 1 | DMF, hydroxylamine free base | 15 | 70 |
| 2 | DMF | 15 | 79 (88)[c] |
| 3 | DMF, ketoacid sodium salt | 15 | 75 |
| 4 | MeOH | 24 | 72 |
| 5 | 5:1 DMF/$H_2O$ | 15 | 72 (77)[c] |
| 6 | DMSO | 15 | 80 |
| 7 | NMP | 15 | 72 |
| 8 | pH 4 acetate buffer | 24 | (70)[c] |
| 9 | 6N $NH_4Cl$, 60° C. | 15 | 68(70)[c] |

[a]All reactions performed on a 0.2 mmol scale.
[b]Isolated yields following chromatography.
[c]HPLC yields of unpurified reaction mixtures.

Simply warming solutions of these compounds led directly to the expected amide (18) in 70% yield after 15 h. Of concern during our reaction screening was the inconvenience of preparing and handling the hydroxylamines in their free base form. We were therefore pleased to find that salts of the hydroxylamine are equally, and possibly more, efficient in the amidation reaction and selected the stable and highly crystalline hydroxylamine monooxalates as practical substrates (entry 2). Likewise, either the protonated ketoacids or their carboxylate salts are suitable reactants (entry 3). Other polar solvents including DMSO, MeOH, and NMP were acceptable (entries 4-7). Furthermore, amide bond formations occurred under aqueous conditions using either suspensions of the reactants in pure $H_2O$, aqueous buffers, or in soluble mixtures of $H_2O$ with DMF as cosolvent. The reactions were typically performed at 0.1 M using 1.0 equiv ketoacid, 1.2 equiv hydroxylamine oxalate at 40° C., but lower concentrations (0.01 M, 0.005 M) and other reactant stoichiometries were viable. Monitoring the reactions by reverse-phase HPLC reveals clean product formation.

With the potential of the ketoacid-hydroxylamine ligation to impact the synthesis of native peptide bonds from polypeptide fragments in mind, we sought to address two critical issues. First, we established the configurational stability of the α-ketoacids over the course of the reaction by preparing substrate 4 in both epimeric and enantioenriched form. Coupling of ketoacid (23) (>15:1 dr by 1H NMR) with (S)—N-hydroxyalanine tert-butyl ester (24) produced the expected amide (25) in 62% isolated yield (Scheme 1).

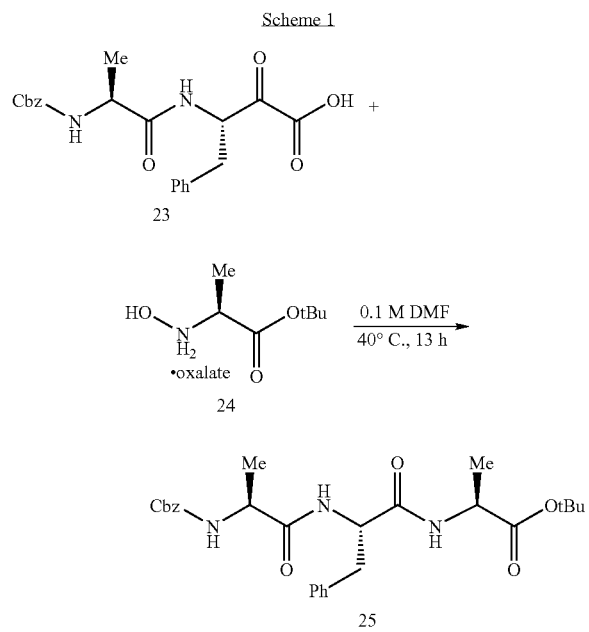

Scheme 1

Comparison of (25) obtained in this manner to the authentic epimeric mixture synthesized from rac-Phe by either traditional coupling reagent based approaches or by ketoacidhydroxylamine couplings, confirmed that the ligation reaction proceeds without significant epimerization (19:1 dr by HPLC). The observation that α-ketoacids are configurationally stable under the reaction conditions is general and we have performed numerous ketoacid-hydroxylamine ligations without erosion of stereochemical integrity. The configuration stability of α-ketoacids is consistent with previous findings. [8]

Second, we confirmed the high tolerance of this process to reactive functional groups including free amines, carboxylic acids, azides, and heterocycles. Working first with protected hydroxylamines we successfully explored reactions with α-ketoacids containing common functionalities, including free lysine and aspartic acid side chains (Scheme 2; Table 2).

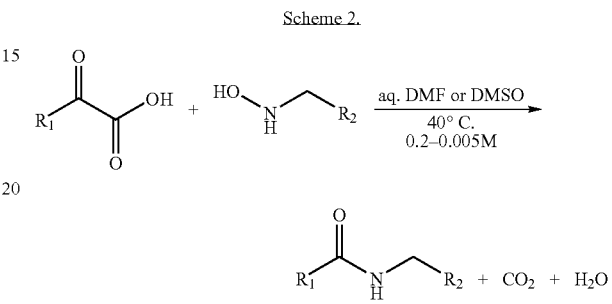

Scheme 2.

TABLE 2

Selected peptide ligation products prepared by the coupling of α-ketoacids and hydroxylamines.

| Structure no. | Product | time[a] (h) | yield[b] (%) |
|---|---|---|---|
| 26 | (structure) | 15 | 62 |
| 27 | (structure) | 15 | 99 |
| 28 | FmocAlaPro-AlaOtBu | 10 | 72 |
| 29 | FmocAlaVal-GlyOEt | 15 | 58 |
| 30 | $H_2$NLysAlaPhe-AlaAsp(tBu)PheOtBu | 15 | 74 |
| 31 | FmocHNAspAlaPhe-AlaAsp(tBu)PheOtBu | 10 | 74 |

We have also demonstrated the potential of this reaction to operate as a peptide ligation on a range of coupling sites including Ala-Ala, Phe-Ala, Val-Gly, Ala-Phe, and Pro-Ala. The use of ketoacids and hydroxylamines derived from amino acids other than glycine is particularly significant as it demonstrates a wide scope in both reaction partners and a tolerance to steric hindrance that compliments existing methods. This process is suitable to many other ligation sites and substrates.

Importantly, fully unprotected hydroxylamines and ketoacids also coupled to give the expected peptide ligation products (Scheme 3). Thus, $H_2$N-Lys-Ala-Phe-COOH (32) reacted with HONH-Ala-Asp-Phe-OH (33) in wet DMF (0.05 M) at 40° C., affording peptide (34) in 75% isolated yield following preparative reverse-phase HPLC. The same experiment performed in pH 5 acetate buffer gave the identical product, albeit at a diminished reaction rate.

Scheme 3

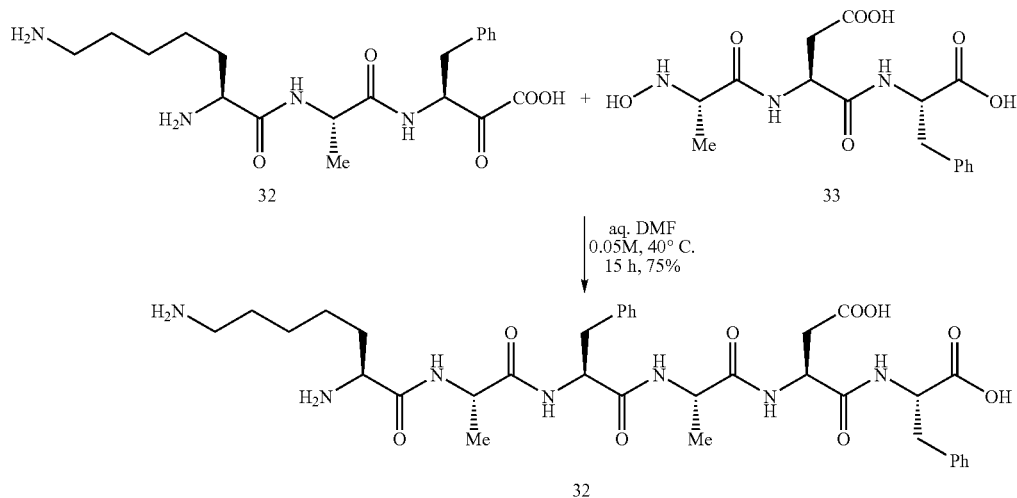

Peptide hydroxylamines are well known compounds [9], readily prepared from N-terminal amines by Fukuyama's method [10]. The resulting side-chain protected peptide hydroxylamines can be deprotected under standard conditions. The preparation of exemplary hydroxylamines is detailed in Example 3.

Existing methods for the synthesis of C-terminal ketoacids [11] are suitable for the preparation of simple substrates and our new process for the synthesis of α-ketoacids, detailed in Example 2, make possible the preparation of larger, fully unprotected, and enantiomerically pure C-terminal ketoacid substrates for ketoacid-hydroxylamine ligations.

The coupling of α-ketoacids and hydroxylamines is a powerful, chemoselective amide bond formation that proceeds in the presence of reactive functional groups and produces only water and $CO_2$ as byproducts. This reaction is useful for the coupling of unprotected molecules and for tandem ligation strategies. [12] Its unique operational paradigm, which does not require reagents for amide bond formation, has further uses in template-directed synthesis.

Example 2

Novel Sulfur Reagent and its Use for Synthesis of α-Ketoacids

We developed a new process for the synthesis of α-ketoacids which employs a novel sulfur reagent that makes possible the preparation of larger, fully unprotected, and enantiomerically pure C-terminal ketoacid substrates for ketoacid-hydroxylamine ligations.

Preparation of Sulfur Reagent:

Equation 2:

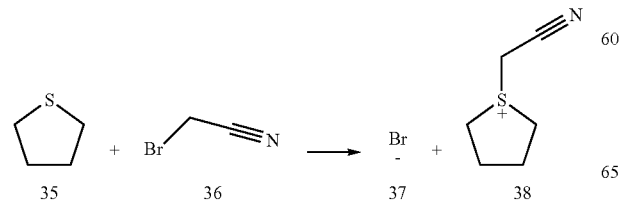

Tetrahydrothiophene (35) is added to a stirring solution of acetone (2 ml/g of sulfide) followed by bromoacetonitrile (36) (1.1 eq). The mixture is allowed to stir for 36-48 hr. The white solid that forms (38) is collected in a filter and washed with acetone and then dried under vacuum. The salt can be used directly in the next reaction:

Formation of Sulfur Ylides

Equation 3:

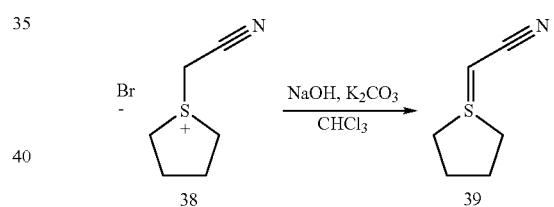

The salt is suspended in $CHCl_3$ (2 ml). Next, $K_2CO_3$ (1.13 ml saturated aqueous solution) and NaOH (0.22 ml, 12N) are added. The mixture is allowed to stir at room temperature for 45 minutes, then filtered over celite, dried over $Na_2SO_4$, filtered, and solvents removed in vacu. The resulting sulfur reagent (39) is best directly used in a subsequent reaction.

Procedure for Sulfur Ylide Coupling to Carboxylic Acids

Equation 4:

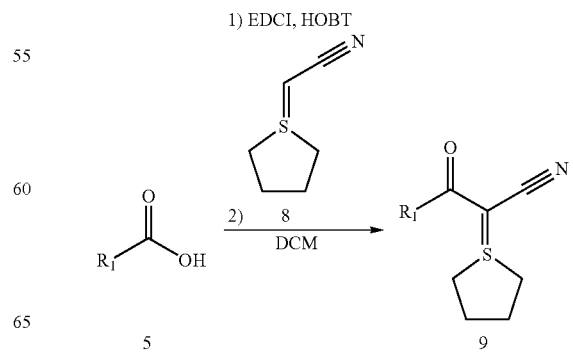

To a solution of a carboxylic acid (5) in DCM (0.2 M) is added HOBT (1.3 eq) and EDCI (1.1 eq) at 0° C. The resulting mixture is allowed to stir at 0° C. for 30 min, then a DCM solution of reagent (8) is added in one portion (2.5 eq) and the resulting solution is let stir at 0° C. for 5 min, then warmed to room temp and stirring continued until completion (usually 15 min to 1 h). The crude mixture is transferred to a separatory funnel and HCl (1N) is added. The resulting layers are partitioned and separated. The aqueous layer is extracted three times with DCM and the resulting organic extracts are combined and dried over Na$_2$SO$_4$, filtered and concentrated under reduced pressure, purification over silica gel affords the desired sulfur ylide product (9). These compounds are extremely polar. Solvent combinations of EtOAc/Acetone/MeOH and DCM are appropriate to get the product off of a column.

Compound 40 is representative:

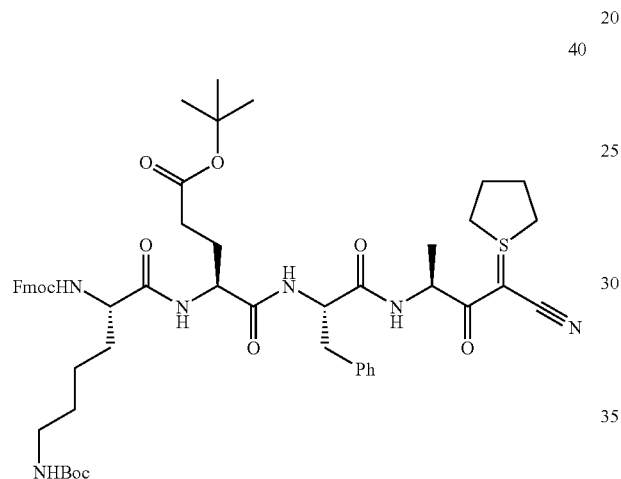

40

The following additional compounds have also been made:

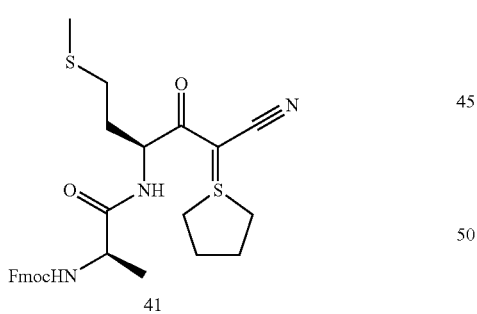

41

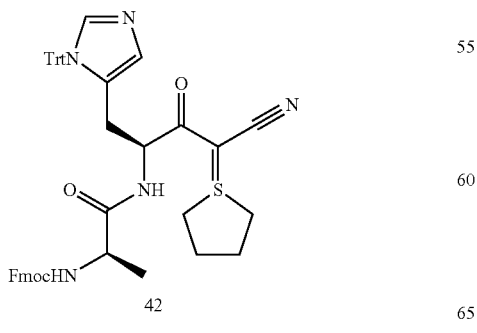

42

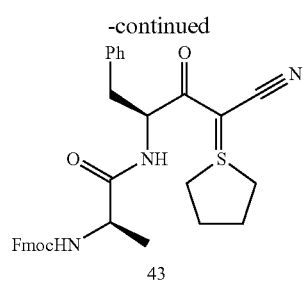

43

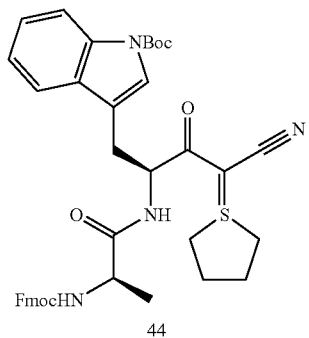

44

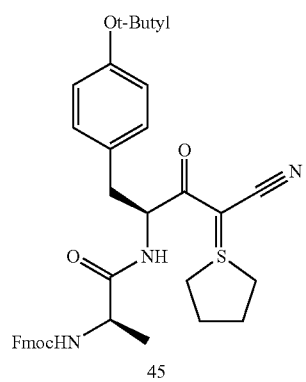

45

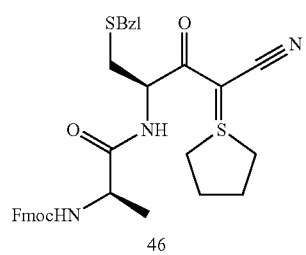

46

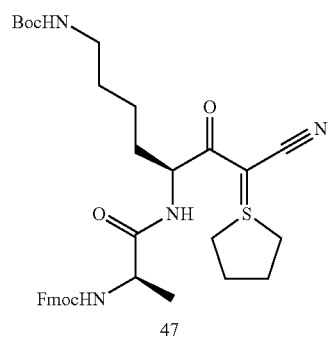

47

-continued

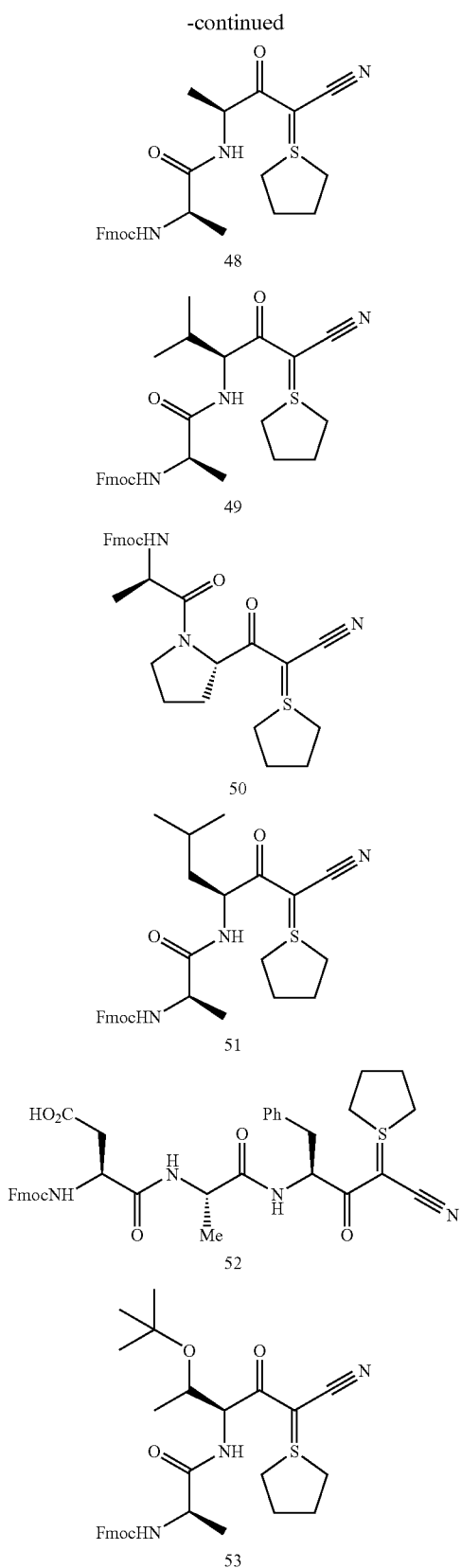

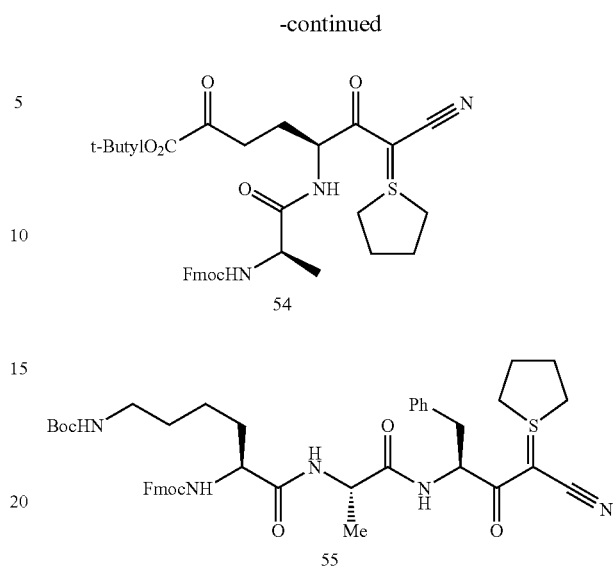

Preparation of α-Ketoacids

Equation 5:

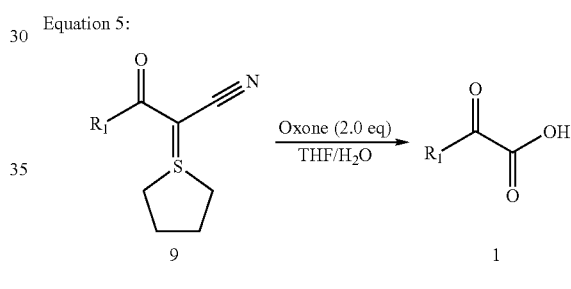

To a solution of a sulfur ylide (9) in THF and water (2:1) is added oxone (2.0 eq). The mixture is allowed to stir until completion. Reaction time varies; however, most substrates are fully oxidized within 1-1.5 h. If there are no free amines present, the crude reaction mixture is then added to a separatory funnel. Dilute HCl is then added followed by EtOAc. The aqueous layer is extracted three times with EtOAc and the combined organic extracts dried over $Na_2SO_4$, filtered, and solvents removed to a minimal volume at which time the solvent of choice is added (DMSO, DMF, $H_2O$), and the remaining volume of volatile solvents removed. The resulting solution contains the desired ketoacid (1) which can be used directly in the next reaction. If the substrate contains free amine groups, then the crude mixture is taken directly to a $C^{18}$ column and purified accordingly.

Notes: on fully protected substrates, 0.1M solutions work the best. If there are free amines present, 0.01M is optimal. If oxidation does not seem to work, add additional Oxone, 0.2 eq at a time until oxidation completion. The reactions are best monitored by reverse phase HPLC.

Representative Reactions and Products:

Scheme 4:

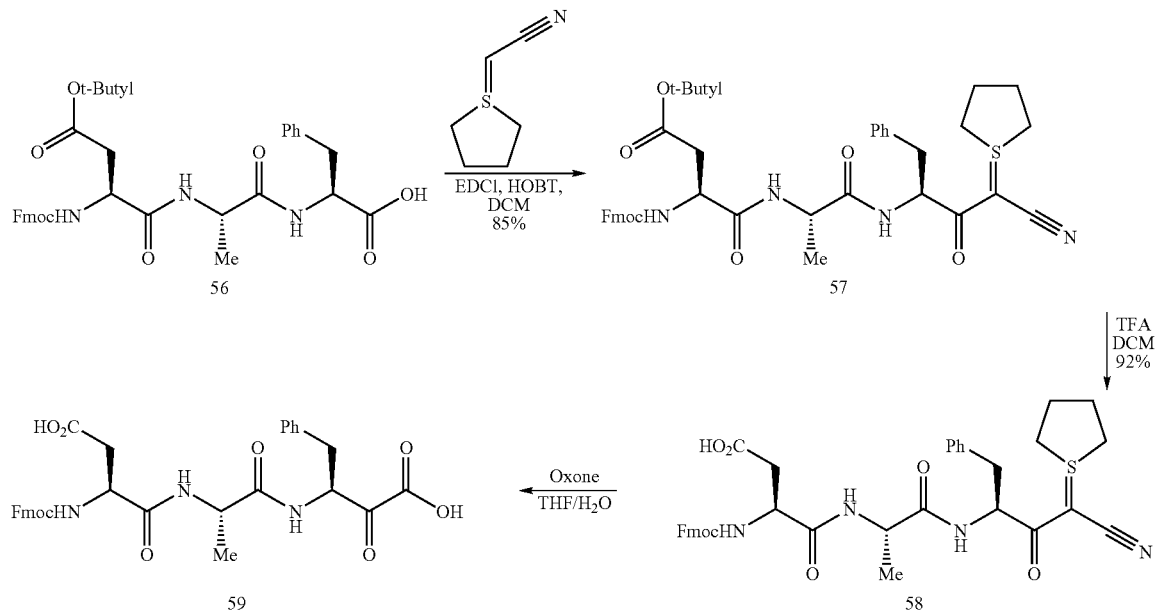

We have also demonstrated that the sulfur ylides are stable and can be Fmoc deprotected and coupled to additional amino acids (Scheme 5). The methodology works very well in the preparation of substrates with Fmoc chemistry with acid labile side chain protections. Ligation reactions can be performed on both protected and unprotected peptide fragments and standard protecting groups do not interfere with the ligation chemistry. Our studies have shown that the α-ketoacids do not epimerize during the ligation step. This is likely due to both the reaction mechanism and the slightly acid media that the ligation reactions are conducted in. Other approaches to the synthesis of the ketoacids are inferior. For example, Wasserman's phosphorous ylide method leads to extensive epimerization (J. Org. Chem. (1994) 59:4364-4366).

Scheme 5:

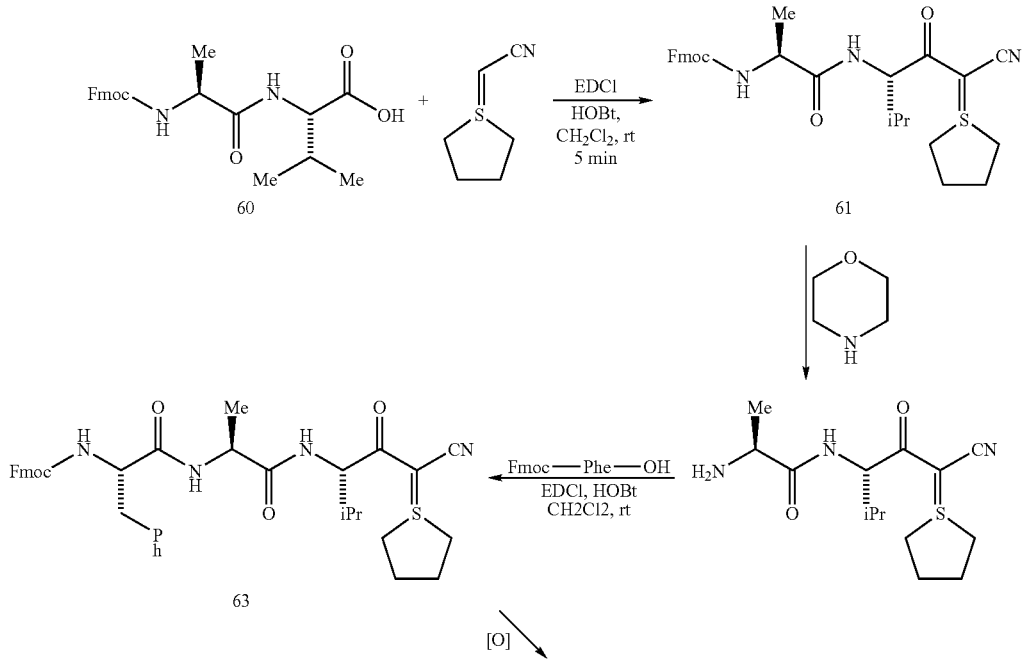

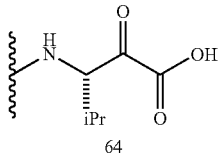

A considerable number of di-, tri-, and tetra peptide ketoacids have been prepared via this approach. Selected substrates include:

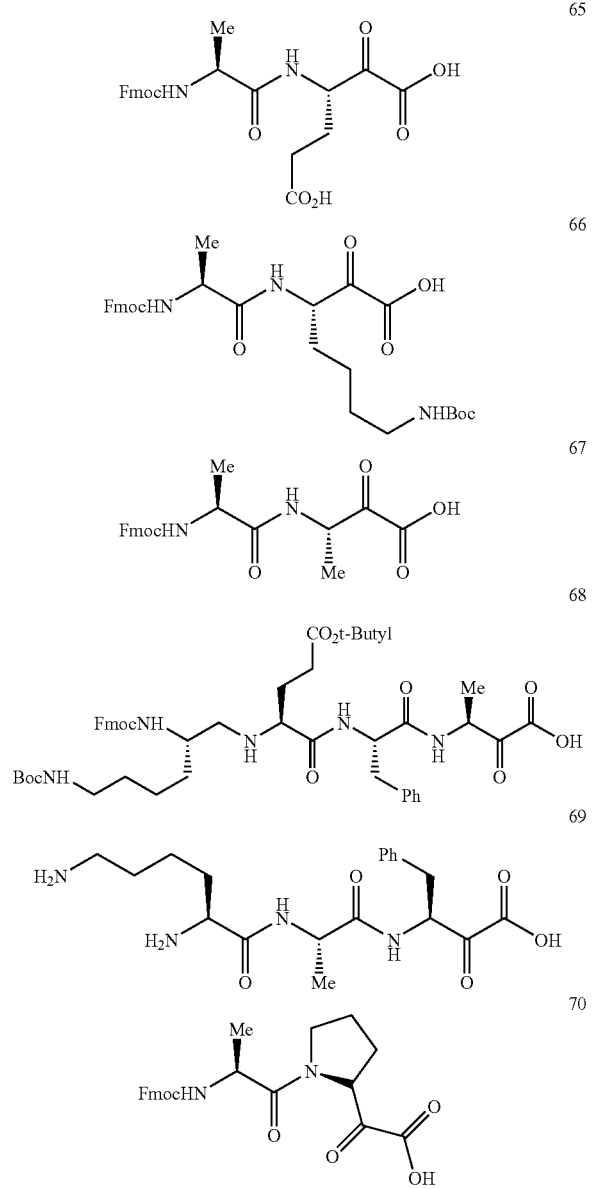

Example 3

Preparation of Amine Reagents

O-Unsubstituted Hydroxylamines

O-unsubstituted hydroxylamines are prepared from fully protected (side chain and C-terminus) N-terminal amino acids or peptides by the method of Fukuyama [10]. The resulting protected hydroxylamines can be fully deprotected under acidic conditions (i.e. TFA). We have also utilized Fukuyama's procedure for the synthesis of N-Boc and N-Fmoc protected N-hydroxyl amino acids suitable for coupling onto the N-terminus of a growing peptide chain. It should be noted that N-hydroxypeptides are well known compounds (for a review: Chem. Rev. 1986, 86, 697-707). Selected hydroxylamines prepared via this methodology include:

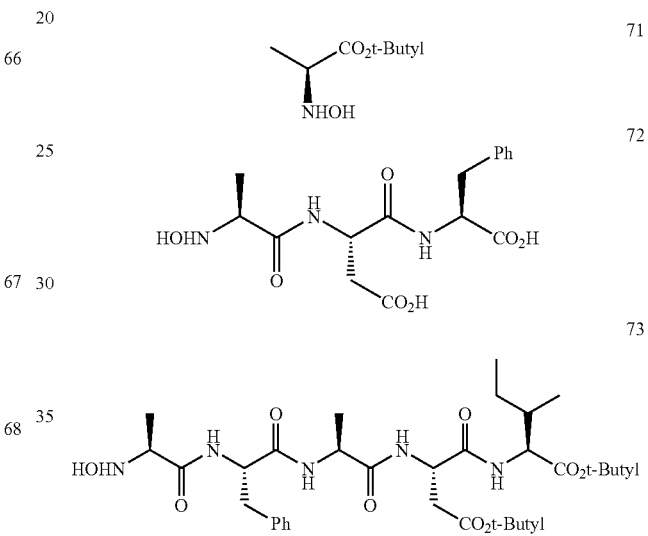

Here we detail the preparation of the above compound 73. To a 10 ml round bottom flask equipped with a stir bar and under argon was added FmocAlaPheAlaAsp(Otbu)Ile(Otbu) (869 mg, 1.01 mmol), DMF (5 ml) and morpholine (2 ml). The mixture was allowed to stir at room temperature for 2 h. After completion, the solvents were removed under reduced pressure. Methanol was then added to the residue and the white precipitate was filtered off and washed with methanol (100 ml). The resulting solution was subject to reduced pressure to remove the methanol, and then toluene was added and removed under vacuum to afford the crude amine. The resulting residue was transferred to a 25 ml round bottom flask equipped with a stir bar and under argon. To the residue was added acetonitrile (10 ml), and DIEA (0.86 ml). The mixture was allowed to stir at room temperature for 5 minutes, at which point bromoacetonitrile (75 µl) was added. The mixture was then heated to 70° C. for 4 h. After completion, the solvents were removed under reduced pressure. To the resulting residue was added $CH_2Cl_2$ (50 ml), and saturated $NaHCO_2$ (50 ml). The solution organic layer was then separated and the resulting aqueous layer was extracted with $CH_2Cl_2$ (50 ml) two more times. The combined organic extracts were then washed with brine, and dried over $Na_2SO_4$, filtered, and solvents removed under reduced pressure. The resulting residue was purified over silica gel, eluting with EtOAc/Hex, 70:30 to afford the desired product (74) in 83% yield:

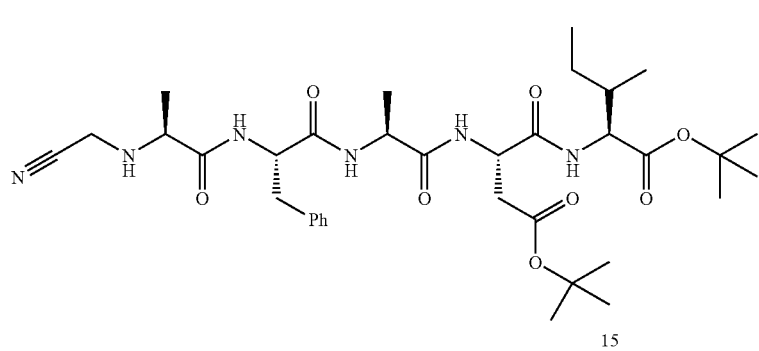

74

To a 25 ml round bottom flask equipped with a stir bar and under argon was added compound 74 (315 mg, 0.46 mmol) and $CH_2Cl_2$ (5 ml). The solution was cooled to 0° C., and MCPBA was added in six portions (48 mg, 0.15 mmol each) in five minute intervals. The mixture was then allowed to warm to room temperature and stir an additional 30 minutes, then cooled to 0° C., and $Na_2S_2O_2$ (145 mg, 0.92 mmol) in water (1 ml), and saturated $NaHCO_2$ (2 ml) was added. Stirring was continued until the mixture became homogeneous at which point $CH_2Cl_2$ was added (30 ml) and $NaHCO_2$ (20 ml) was added. The two phases were separated and the aqueous phase extracted with three times with $CH_2Cl_2$ (30 ml). The combined organic extracts were then washed with brine, dried over $Na_2SO_2$, filtered, and solvents removed under reduced pressure. The residue was purified over silica gel eluting with EtOAc/Hex, 80/20 to afford the desired product in 89% (75) yield:

75

To a 25 ml round bottom flask was added compound 42 (280 mg, 0.4 mmol) and MeOH (10 ml), To this solution was then added hydroxylamine hydrochloride (138 mg, 2.0 mmol). The solution was heated to 50° C. for 8 hr, and then cooled to room temperature. After cooling, $CH_2Cl_2$ (10 ml) was added and stirring continued for an additional five minutes. To the resulting solution was added saturated $NaHCO_3$, and the aqueous layer extracted 3 times with $CH_2Cl_2$. The combined organic extracts were washed with brine, dried over $Na_2SO_4$, filtered and solvents removed under reduced pressure. To the residue was added oxalic acid (100 mg, 0.80 mmol) in MeOH (1 ml). The product was crystallized by addition of $Et_2O$ to the residue then filtered to give 240 mg of compound 73 (80%).

O-Substituted Hydroxylamines

We have prepared N-methoxy peptides by the reaction of alpha-bromoacetyl terminated peptide chains with commercially available O-methylhydroxylamine hydrochloride (eq. 6):

Equation 6:

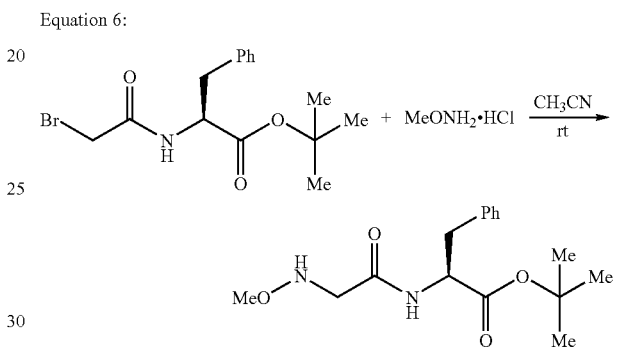

Isoxazolidines

We have synthesized isoxazolidines which can be used for beta-peptide synthesis using methodology outlined in the following Scheme 6:

-continued

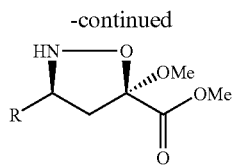

a) 10 mol % dibutylin oxide, toluene, reflux; b) MeOH, aq. HClO₄, refulx

Using this scheme, methyl 5-methoxy-3-p-tolylisoxazolidine-5-carboxylate (80) was prepared as detailed below.

Step 1: Compound 76 (3 g, 25 mmol, 1 equiv) was dissolved in benzene (64 mL). To this solution, p-tolualdehyde (3 mL, 25 mmol, 1 equiv) and dibutyltin oxide (0.32 g, 1.1 mmol, 0.05 equiv) were added. The reaction mixture was refluxed with a dean stark trap at 95° C. for 1 day. The solvent was rotoevaporated and the product was purified by column chromatography (3:1 hexanes/EtOAc) to afford 78 (3.3 g, 58.8%) as a viscous yellow liquid:

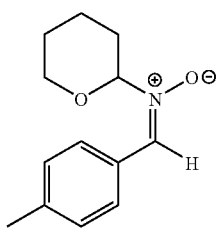

78

Step 2: To a solution of 78 (3 g, 13.6 mmol, 1 equiv) in toluene (150 mL) was added 77 (1.58 g, 13.6 mmol, 1 equiv). The reaction mixture was refluxed at 95° C. for 2 days. The solvent was rotoevaporated and the resulting product was purified by column chromatography (5:1 hexanes/EtOAc) to give 79 (1.7 g, 5.07 mmol, 37.3%) as a viscous yellow liquid:

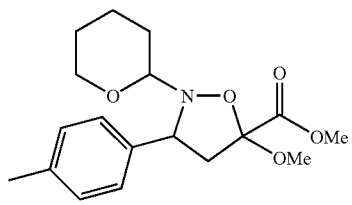

79

Note: steps 2 and 3 may also be combined together in the same reaction vessel.

Step 3: To a solution of 79 (1.2 g, 3.58 mmol, 1 equiv) in MeOH (50 mL) was added HClO₄ (0.75 g, 7.47 mmol, 2 equiv). The reaction mixture was refluxed at 65° C. for 4 hours. Then DI H₂O (50 mL) and a saturated aqueous solution of sodium bicarbonate (20 mL) were added to the reaction mixture. The solution was extracted using EtOAc (3×50 mL). The combined organic layers were washed with brine and then dried with Na₂SO₄. The solvent was rotoevaporated and the resulting product was purified by column chromatography (3:1 hexanes/EtOAc) to give 80 (0.65 g, 2.6 mmol, 72%) as a viscous yellow liquid:

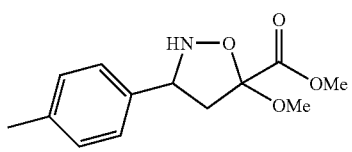

80

Many variations of this procedure are possible. We often perform steps 1 and 2 simultaneously by mixing everything. The use of the dibutyltin oxide catalyst is not necessary. Also, it may be substituted by other reagents including Na₂SO₄ or Mg₂SO₄ or molecular sieves. The procedure above uses an achiral hydroxylamine for synthesizing the nitrone. We have also used chiral hydroxylamines derived from D-mannose or L-ribose. The use of these nitrones has been reported by other researchers, but not for the synthesis of these specific compounds. For selected references, see Vasella, A. *Helv. Chim. Acta.* 1977, 60, 1273; and Kasahara, K.; Iida, H.; Kibayashi, C. *J. Org. Chem.* 1989, 54, 2225-2233.

Additional Amine Reagents:

Any one of a variety of amine reagents can be used in the decarboxylative condensation reaction with the α-ketoacid. Non-limiting examples include:

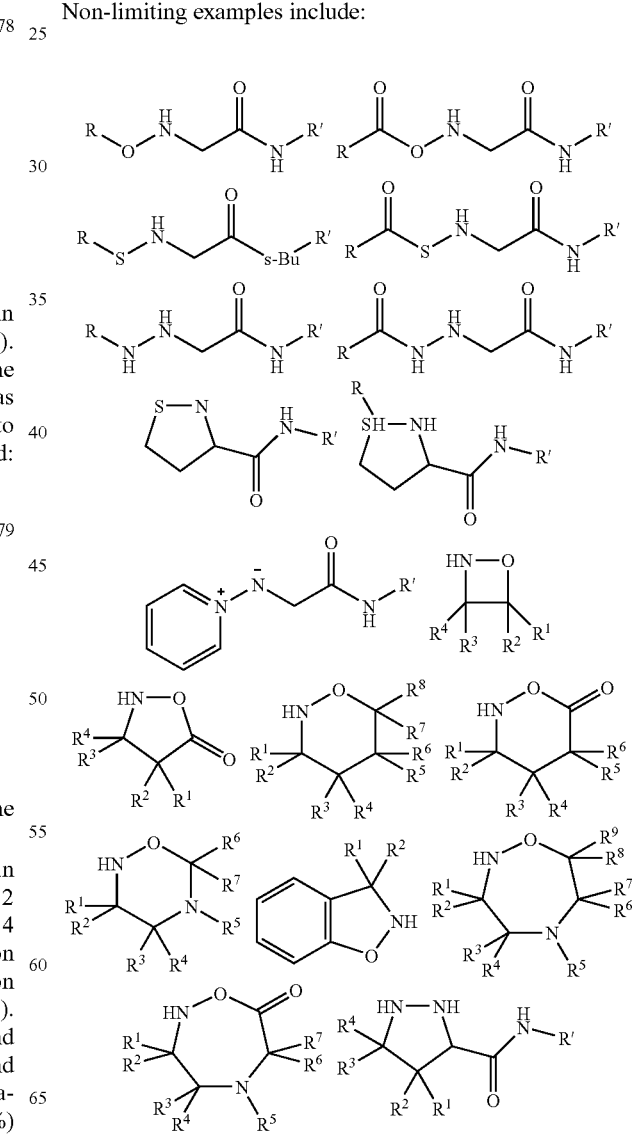

wherein the R groups (i.e. R, R', and $R^{1-9}$) are independently selected from hydrogen, alkyl (particularly methyl, ethyl, isopropyl, isobutyl, benzyl), an aromatic group, acyl, oxyalkyl, amino alkyl, thioalkyl, and alkyl siloxanes.

The foregoing examples and detailed description are offered by way of illustration and not by way of limitation. All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims

REFERENCES

[1] Jones, J. The Chemical Synthesis of Peptides; Clarendon Press: Oxford 1991.
[2] (a) Schnölzer, M.; Kent, S. B. H. Science 1992, 256, 221-225. (b) Kochendoerfer, G. G.; Kent, S. B. H. Curr. Opin. Chem. Biol. 1999, 3, 665-671.
[3] Yan, L. Z.; Dawson, P. E. J. Am. Chem. Soc. 2001, 123, 526-533.
[4] For Staudinger ligations, see: (a) Nilsson, B. L.; Hondal, R. J.; Soellner, M. B.; Raines, R. T. J. Am. Chem. Soc. 2003, 125, 5268-5269. (b) Nilsson, B. L. Kiessling, L. L.; Raines, R. T. Org. Lett. 2000, 3, 9-12. (c) Saxon, E.; Armstrong, J.; Bertozzi, C. R. Org. Lett. 2000, 3, 2141-2143.
[5] For thioacid-azide ligations, see: (a) Shangguan, N.; Katukojvala, S.; Greenberg, R.; Williams, L. J. J. Am. Chem. Soc. 2003, 125, 7754-7755. (b) Fazio, F.; Wong, C.-H. Tetrahedron Lett. 2003, 44, 9083-9085.
[6] Ishikawa, T.; Nagai, K.; Senzaki, M.; Tatsukawa, A.; Saito, S. Tetrahedron 1998, 54, 2433-2448.
[7] For the synthesis of other carboxylic acid derivatives by oxidative decarboxylations of α-ketoacids, see: Beebe, T. R. et al. J. Org. Chem. 1987, 52, 3165-3166. (b) Corbett, M. D.; Corbett, B. R., J. Org. Chem. 1980, 45, 2834-2839.
[8] Cooper, A. J. L.; Ginos, J. Z.; Meister, A. Chem. Rev. 1983, 83, 321-358.
[9] Ottenheijm, H. C. J.; Herscheid, J. D. M. Chem. Rev. 1986, 86, 697-707.
[10] Tokuyama, H.; Kuboyama, T.; Amano, A.; Yamashita, T.; Fukuyama, T. Synthesis 2000, 1299-1304.
[11] Wasserman, H. H.; Ho, W.-B. J. Org. Chem. 1994, 59, 4364-4366.
[12] Tam, J. P.; Yu, Q.; Lu, Y.-A. Biologicals 2001, 29, 189-196.
[13] Liu, R.; Orgel, L. E. Nature 1997, 389, 52-54.

What is claimed is:

1. A method of forming an amide, the method comprising the step of:
reacting an α-ketoacid or salt thereof in a decarboxylative condensation reaction with an amine or salt thereof wherein the amine has the structure of formula (2):

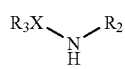

(2)

wherein $R_2$ is selected from optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety;

X is selected from an oxygen atom, a nitrogen atom, and a sulfur atom; and $R_3$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, and a bond that joins X to $R_2$ that, taken together with the nitrogen atom, forms a optionally substituted heterocyclic ring of 4 to 7 atoms;
whereby an amide bond is formed between the α-carbon of the ketoacid and the nitrogen of the amine.

2. A method of forming an amide, the method comprising the step of:
reacting an α-ketoacid or salt thereof in a decarboxylative condensation reaction with an amine or salt thereof comprising a nitrogen covalently bound to an atom selected from oxygen, nitrogen, and sulfur;
whereby an amide bond is formed between the α-carbon of the ketoacid and the nitrogen of the amine, wherein the α-ketoacid has the structure of formula (1):

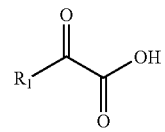

(1)

the amine has the structure of formula (2):

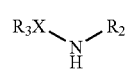

(2)

and the amide has the structure of formula (3):

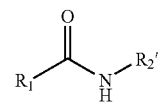

(3)

wherein $R_1$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety;

$R_2$ is selected from optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety;

X is selected from an oxygen atom, a nitrogen atom, and a sulfur atom;

$R_3$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, and a bond that joins X to $R_2$ that, taken together with the nitrogen atom, forms a optionally substituted heterocyclic ring of 4 to 7 atoms; and $R_2'$ is $R_2$ or, when $R_3$ is a bond, the ring-opening reaction product of $R_2$.

3. The method of claim 1 wherein the amine has the structure of formula (4):

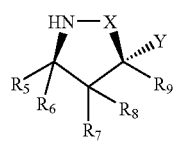

(4)

wherein X is selected from an oxygen atom, a nitrogen atom, and a sulfur atom;

Y is selected from hydrogen, optionally hetero-, optionally substituted alkyl, optionally hetero-, optionally substituted arylalkyl, optionally hetero, optionally substituted aryl, optionally substituted oxyalkyl, optionally hetero-, optionally substituted oxyaryl, optionally hetero-, optionally substituted thioalkyl, and optionally hetero-, optionally substituted thioaryl; and $R_5$ through $R_9$ are independently selected from hydrogen, optionally hetero, optionally substituted alkyl, optionally hetero, optionally substituted aryl, optionally hetero, optionally substituted acyl, oxygen, nitrogen, and a bond that joins with a different one of said $R_5$ through $R_9$ to form a ring.

4. The method of claim 1 wherein the amine is an isoxazolidine.

5. The method of claim 1 wherein the amine is selected from the group consisting of an N-alkylhydroxylamine, an N,O-dialkylhydroxylamine, an N-alkyl, O-acylhydroxylamine, and a peptide hydroxylamine.

6. The method of claim 1 wherein the reaction is not dependent upon additional reagent or catalyst.

7. The method of claim 1 wherein the principal by-products produced by the reaction are water and $CO_2$.

8. The method of claim 1 wherein the principal by-products produced by the reaction are an alcohol and $CO_2$.

9. The method of claim 1 wherein the reaction occurs at 0° C.-150° C.

10. The method of claim 1 wherein the reaction occurs at 25° C.-75° C.

11. The method of claim 1 wherein the reaction occurs on a solid phase.

12. The method of claim 1 wherein prior to the reacting step, the α-ketoacid is synthesized by combining a carboxylic acid of formula (5):

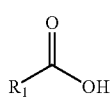

(5)

with a sulfur reagent of formula (6):

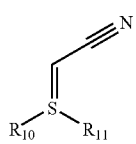

(6)

or a salt thereof under reaction conditions to form a sulfur ylide of formula (7):

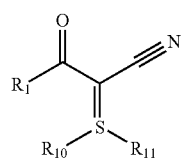

(7)

and contacting the sulfur ylide with an oxidizer and water to form the α-ketoacid;

wherein $R_1$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety;

$R_{10}$ is selected from optionally hetero-, optionally substituted alkyl, and optionally hetero-, optionally substituted aryl; and $R_{11}$ is selected from optionally hetero-, optionally substituted alkyl, optionally hetero-, optionally substituted aryl, and a bond that joins $R_{10}$ to form an optionally substituted heterocyclic ring of 4 to 7 atoms.

13. The method of claim 2 wherein the amine has the structure of formula (4):

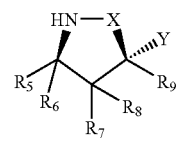

(4)

wherein X is selected from an oxygen atom, a nitrogen atom, and a sulfur atom;

Y is selected from hydrogen, optionally hetero-, optionally substituted alkyl, optionally hetero-, optionally substituted arylalkyl, optionally hetero, optionally substituted aryl, optionally substituted oxyalkyl, optionally hetero-, optionally substituted oxyaryl, optionally hetero-, optionally substituted thioalkyl, and optionally hetero-, optionally substituted thioaryl; and $R_5$ through $R_9$ are independently selected from hydrogen, optionally hetero, optionally substituted alkyl, optionally hetero, optionally substituted aryl, optionally hetero, optionally substituted acyl, oxygen, nitrogen, and a bond that joins with a different one of said $R_5$ through $R_9$ to form a ring.

14. The method of claim 2 wherein the amine is an isoxazolidine.

15. The method of claim 2 wherein the amine is selected from the group consisting of an N-alkylhydroxylamine, an N,O-dialkylhydroxylamine, an N-alkyl, O-acylhydroxylamine, and a peptide hydroxylamine.

16. The method of claim 2 wherein the reaction is not dependent upon additional reagent or catalyst.

17. The method of claim 2 wherein the principal by-products produced by the reaction are water and $CO_2$.

18. The method of claim 2 wherein the principal by-products produced by the reaction are an alcohol and $CO_2$.

19. The method of claim 2 wherein the reaction occurs at 0° C.-150° C.

20. The method of claim 2 wherein the reaction occurs at 25° C.-75° C.

21. The method of claim 2 wherein the reaction occurs on a solid phase.

22. The method of claim 2 wherein prior to the reacting step, the α-ketoacid is synthesized by combining a carboxylic acid of formula (5):

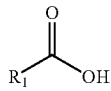
(5)

with a sulfur reagent of formula (6):

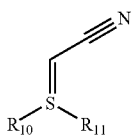
(6)

or a salt thereof under reaction conditions to form a sulfur ylide of formula (7):

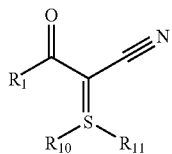
(7)

and contacting the sulfur ylide with an oxidizer and water to form the α-ketoacid;

wherein $R_1$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety;

$R_{10}$ is selected from optionally hetero-, optionally substituted alkyl, and optionally hetero-, optionally substituted aryl; and $R_{11}$ is selected from optionally hetero-, optionally substituted alkyl, optionally hetero-, optionally substituted aryl, and a bond that joins $R_{10}$ to form an optionally substituted heterocyclic ring of 4 to 7 atoms.

23. The method of claim 2 wherein the α-ketoacid has the structure of formula (1):

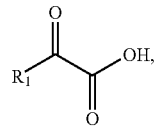
(1)

the amine has the structure of formula (2):

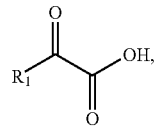
(2)

and the amide has the structure of formula (3):

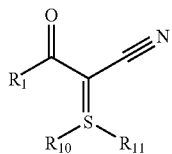
(3)

wherein $R_1$ is selected from hydrogen, optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety; and $R_2$ is selected from optionally hetero-, optionally substituted alkyl, optionally hetero-, optionally substituted alkenyl, optionally hetero-, optionally substituted alkynyl, optionally hetero-, optionally substituted aryl, optionally hetero-, optionally substituted arylalkyl, optionally hetero-, optionally substituted acyl, a carbohydrate moiety, an amino acid moiety, a peptide moiety, a nucleotide moiety, a nucleoside moiety, and a peptide nucleic acid moiety.

24. The method of claim 1 wherein the amide is a peptide.
25. The method of claim 2 wherein the amide is a peptide.
26. The method of claim 23 wherein the amide is a peptide.
27. The method of claim 1 wherein the α-ketoacid and amine are derivatives of amino acids, and peptide ligation is achieved by directly coupling the α-ketoacid and amine in a decarboxylative condensation reaction and thereby provide a native peptide bond in a peptide.
28. The method of claim 27, wherein the coupling occurs under mild, reagent-free conditions, producing only carbon dioxide and water or alcohol as by-products.

* * * * *